(12) United States Patent (10) Patent No.: US 7,265,825 B2
Kotani (45) Date of Patent: Sep. 4, 2007

(54) APPARATUS FOR MEASURING FLUORESCENCE LIFETIME

(75) Inventor: Tadashi Kotani, Tokyo (JP)

(73) Assignee: Olympus Corporation, Tokyo (JP)

( * ) Notice: Subject to any disclaimer, the term of this patent is extended or adjusted under 35 U.S.C. 154(b) by 435 days.

(21) Appl. No.: 10/769,135

(22) Filed: Jan. 30, 2004

(65) Prior Publication Data

US 2005/0072936 A1 Apr. 7, 2005

(30) Foreign Application Priority Data

Oct. 7, 2003 (JP) ............................ 2003-348615

(51) Int. Cl.
*G01N 21/64* (2006.01)
(52) U.S. Cl. .................................... 356/318; 250/458.1
(58) Field of Classification Search ................ 356/317, 356/318, 417; 250/458.1, 459.1, 461.1, 461.2
See application file for complete search history.

(56) References Cited

U.S. PATENT DOCUMENTS 4,591,984 A 5/1986 Mori
6,690,463 B2 * 2/2004 Kask .......................... 356/317

FOREIGN PATENT DOCUMENTS

| GB | 2 382 648 A | 6/2003 |
| JP | 11-037850 A | 2/1999 |
| JP | 2002-543414 A | 12/2002 |
| JP | 2003-202292 A | 7/2003 |
| JP | 2003-522946 A | 7/2003 |
| WO | WO 03/050518 A2 | 6/2003 |

OTHER PUBLICATIONS

C.J. De Grauw et al; "Multiple Time-Gate Module for Fluorescence Lifetime Imaging"; Applied Spectroscopy; vol. 55, No. 6, 2001; pp. 670-678.
D.J.S. Birch et al; "Array Fluorometry: The Theory of the Statistical Multiplexing of Single Photon Timing"; Time-Resolved Laser Spectroscopy in Biochemistry II, SPIE vol. 1204; 1990. pp. 26-34.
Keller, R. A. et al. "Single-Molecule Fluorescence Analysis in Solution" Applied Spectroscopy, The Society for Applied Spectroscopy. Baltimore, U.S. vol. 50, No. 7, pp. 12A-32A, XP000642337, ISSN: 0003-7028, Jul. 1996.

* cited by examiner

*Primary Examiner*—F. L. Evans
(74) *Attorney, Agent, or Firm*—Frishauf, Holtz, Goodman & Chick, P.C.

(57) ABSTRACT

An apparatus for measuring fluorescence lifetime includes a pulse laser source that generates a pulse excitation light, a detector that detects a fluorescence generated from a sample by irradiating the pulse excitation light, and outputs a detection signal corresponding to the fluorescence, a measurement unit that measures number of photons emitted in a predetermined time gate based on the detection signal, a correction unit that corrects the number of photons measured based on Poisson distribution, and a calculation unit that calculates the fluorescence lifetime of the sample based on the number of photons corrected.

4 Claims, 4 Drawing Sheets

APPARATUS FOR MEASURING FLUORESCENCE LIFETIME

CROSS-REFERENCE TO RELATED APPLICATIONS

The present document incorporates by reference the entire contents of Japanese priority document, 2003-348615 filed in Japan on Oct. 7, 2003.

BACKGROUND OF THE INVENTION

1) Field of the Invention

The present invention relates to an apparatus for measuring fluorescence lifetime based on number of measured photons generated from a sample by irradiating an excitation light on the sample.

2) Description of the Related Art

Recently, researches on methods of calculating fluorescence lifetime of various samples are so popular that lots of methods have been proposed. By irradiating an excitation light on a sample, the molecular state of the sample becomes excited, and a fluorescence is generated while the sample returns to a ground state. The method measures the fluorescence and calculates the fluorescence lifetime to investigate type or state of the sample. One of the methods employs a pulse excitation light to irradiate the sample, and measures the number of photons emitted from the sample in plural time gates (hereinafter, "time gate method). The fluorescence lifetime is calculated based on the number of photons measured in the plural time gates. The time gate method can offer a fluorescence lifetime with a small error if time gates are properly set.

In the time gate method, however, since the probability of emitting photons is generally low, it is required to irradiate the pulse excitation light a number of times. Consequently, it takes an extremely long time to measure the number of photons with reliability. On the other hand, if one increases the probability of emitting photons and sets the time gates to time windows where the probability of emitting photons is high to shorten the time for the measurement, a measurement error becomes large because it is difficult to discriminate each photon when a plurality of photons are incident in the same time gate. For this reason, it is required to measure the number of photons at a very low emission probability where an average of the number of photons being incident in each of the time gates with a single irradiation of pulse excitation light is approximately 0.01 to reduce the measurement error. As a result, for a single calculation of the fluorescence lifetime, at least several ten-thousand-times of irradiation of pulse excitation light is required, and it takes a considerable amount of time to calculate the fluorescence lifetime. In addition, the fluorescence lifetime may change with time even in the same sample. In this case, the time gate method cannot be applied, and a time-dependent fluorescence lifetime change cannot be measured.

SUMMARY OF THE INVENTION

The apparatus for measuring fluorescence lifetime, according to one aspect of the present invention includes a correction unit that acquires a first number of photons emitted from a sample excited by a pulse excitation light, and corrects the first number of photons into a second number of photons based on a predetermined probability distribution, and a calculation unit that calculates the fluorescence lifetime based on the second number of photons.

The apparatus for measuring fluorescence lifetime, according to another aspect of the present invention includes a correction unit that acquires a first number of photons emitted from a sample excited by a pulse excitation light, and corrects the first number of photons into a second number of photons based on Poisson distribution, and a calculation unit that calculates the fluorescence lifetime based on the second number of photons.

The apparatus for measuring fluorescence lifetime, according to still another aspect of the present invention includes a pulse laser source that generates a pulse excitation light, an optical system that irradiates the pulse excitation light to a sample, a detector that detects a fluorescence generated from the sample, and outputs a detection signal corresponding to the fluorescence, a measurement unit that measures a first number of photons emitted from the sample in a predetermined time gate based on the detection signal, a correction unit that corrects the first number of photons into a second number of photons incorporating the first number of photons and number of irradiation times of the pulse excitation light, and a calculation unit that calculates the fluorescence lifetime of the sample based on the second number of photons.

The method of measuring fluorescence lifetime, according to still another aspect of the present invention includes measuring a first number of photons emitted from a sample excited by a pulse excitation light, correcting the first number of photons into a second number of photons based on a predetermined probability distribution, and calculating the fluorescence lifetime based on the second number of photons.

The other objects, features, and advantages of the present invention are specifically set forth in or will become apparent from the following detailed descriptions of the invention when read in conjunction with the accompanying drawings.

DETAILED DESCRIPTION

Exemplary embodiments of an apparatus for measuring fluorescence lifetime according to the present invention are described in detail with reference to the accompanying drawings.

Figure 1:
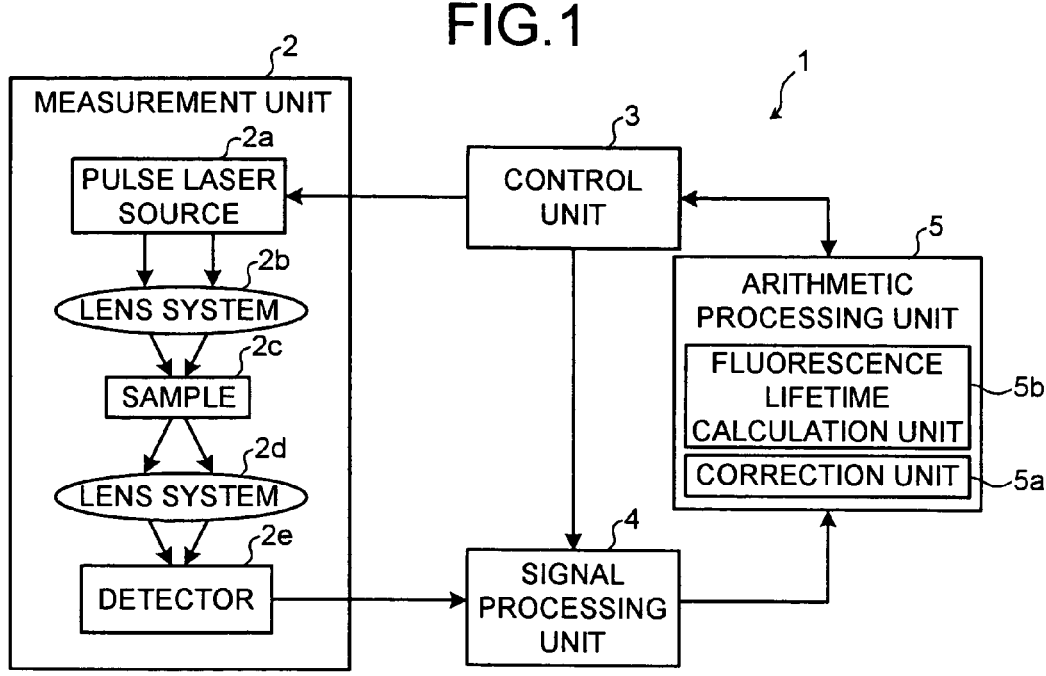
FIG. 1 is a schematic diagram of a fluorescence lifetime measurement apparatus according to an embodiment of the present invention.

FIG. 1 is a schematic diagram of a fluorescence lifetime measurement apparatus 1 according to an embodiment of the present invention. The fluorescence lifetime measurement apparatus 1 includes a measurement unit 2 that irradiates an excitation light on a sample to generate photons and detects the photons generated, a signal processing unit 4 that measures number of photons in plural time gates based on signals of the photons detected, an arithmetic processing unit 5 that calculates the fluorescence lifetime based on the number of photons measured in the plural time gates, and a control unit 3 that controls the measurement unit 2, the signal processing unit 4, and the arithmetic processing unit 5. The control unit 3 controls an emission timing of a pulse laser source 2a, time windows of the plural time gates, and processing of the arithmetic processing unit 5.

The fluorescence lifetime measurement apparatus 1 includes the pulse laser source 2a, lens systems 2b and 2d, a sample 2c, and a detector 2e. Pulse excitation light emitted from the pulse laser source 2a is focused on the sample 2c by the lens system 2b. The sample 2c is excited by the pulse excitation light to be set in an excited state. In transition from the excited state to a ground state, the sample 2c emits photons with a predetermined probability distribution. The photons emitted from the sample 2c are condensed on the detector 2e by the lens system 2d. The detector 2e converts the photons into electric signals and outputs the electric signals to the signal processing unit 4. The signal processing unit 4 measures the number of photons in the plural time gates based on the electric signals and outputs the number of photons to the arithmetic processing unit 5.

Figure 2:
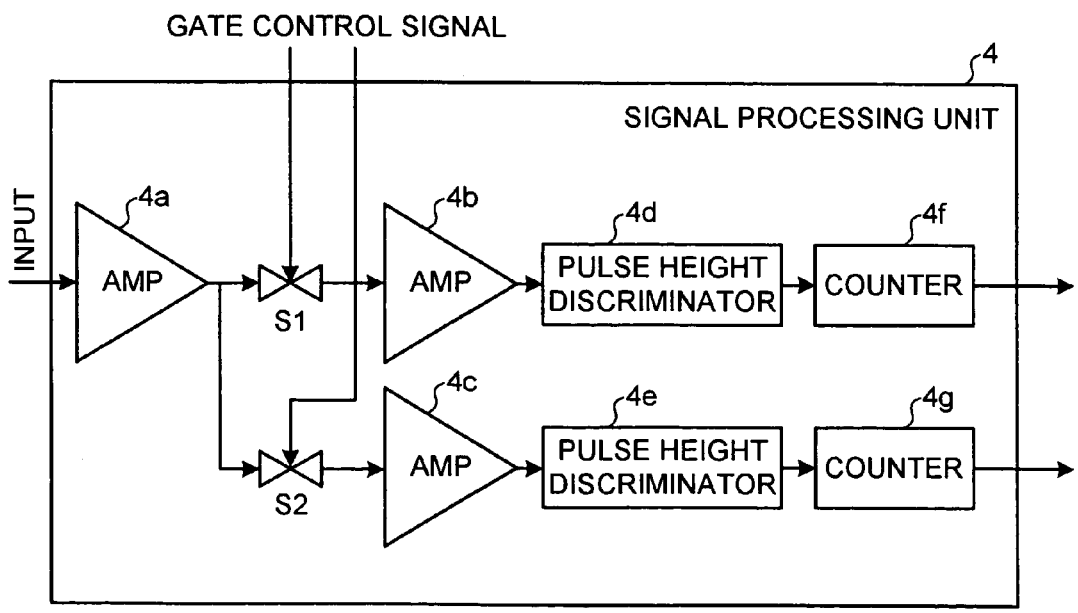
FIG. 2 is a block diagram of a signal processing unit of the fluorescence lifetime measurement apparatus according to the embodiment.

FIG. 2 is a block diagram of the signal processing unit 4 of the fluorescence lifetime measurement apparatus according to the embodiment. In this embodiment, two time gates are used. The signal processing unit 4 includes amplifiers 4a, 4b, and 4c, time gate switches S1 and S2, pulse height discriminators 4d and 4e, and counters 4f and 4g. The signal processing unit 4 amplifies the electric signals input from the detector 2e through the amplifier 4a and branches the electric signals through the time gate switches S1 and S2. The time gate switches S1 and S2 control timings of "ON" and "OFF" operations by a gate control signal from the control unit 3 and output the electric signals to the pulse height discriminators 4d and 4e via the amplifiers 4b and 4c in only an "ON" state. The periods of time of the "ON" operations of the time gate switches S1 and S2 correspond to the time gates, respectively. The pulse height discriminators 4d and 4e binarize the input electric signals by a predetermined time and output the binarized signals to the counters 4f and 4g, respectively. The counters 4f and 4g receive the binary signals, measure the number of photons in the time gates such that one photon is measured when the signal is input, and output the number of measured photons to the arithmetic processing unit 5.

The arithmetic processing unit 5 detects the number of photons measured in the plural time gates set by the control unit 3 based on the number of photons input from the signal processing unit 4 in the time gates and calculates a fluorescence lifetime based on the number of photons in the time gates.

The arithmetic processing unit 5 includes a correction unit 5a and a fluorescence lifetime calculation unit 5b. The correction unit 5a corrects the number of photons measured in the plural time gates to output the number of photons corrected to the fluorescence lifetime calculation unit 5b. The fluorescence lifetime calculation unit 5b calculates the fluorescence lifetime based on the number of photons corrected.

In general, the probability of emitting photons in a transition process from an excited state to a ground state is based on a Poisson distribution. When energy of the pulse excitation light is increased, the probability of emitting photons becomes high. As described above, an error of measurement easily occurs in the number of photons.

Conventionally, in order to avoid such measurement error, the energy of the pulse excitation light is reduced to a predetermined value to make the probability of emitting photons low. For this reason, a large amount of time is required to calculate a fluorescence lifetime.

According to the embodiment, the distribution of the measured number of photons is corrected based on the Poisson distribution. For this reason, even though the number of photons are measured such that time gates each having a high probability of emitting photons are set, a fluorescence lifetime can be calculated within a short period of time with a small measurement error.

The correction is performed such that a distribution of the number of photons input from the signal processing unit 4 and measured in plural time gates with respect to time follows the Poisson distribution. With reference to photons emitted from the sample 2c, in one irradiation of pulse excitation light, when the average number of photons being incident in a predetermined time gate $\Delta T$ is represented by $\mu$, a probability $p(r, \mu)$ of r photons being incident in the time gate $\Delta T$ can be expressed by:

$$p(r, \mu) = \frac{e^{-\mu} \cdot \mu^r}{r!} \quad (1)$$

When r is 1 or more, (1) becomes:

$$p(r \geq 1, \mu) = 1 - e^{-\mu} \quad (2)$$

Pulse excitation light is irradiated N times, and the number of photons measured in a time gate $\Delta T$ is represented by k. In this case, the average number of photons (count rate) x measured per irradiation of pulse excitation light in the time gate $\Delta T$ is given by $x = k/N$. On the other hand, a probability $p(0, \mu)$ of no photon being incident in the time gate $\Delta T$ can be expressed by (3) by using the count rate x.

$$p(0, \mu) = (N-k)/N = 1 - x \quad (3)$$

Similarly, the probability $p(0, \mu)$ of no photon incident in the time gate $\Delta T$ can be expressed by (4) from (1).

$$p(0, \mu) = e^{-\mu} \quad (4)$$

From (3) and (4), the average number $\mu$ of photons being incident in the time gate $\Delta T$ can be expressed by:

$$\mu = -\ln(1-x) \quad (5)$$

Therefore, when the number of photons being incident in the time gate $\Delta T$ is represented by m, as expressed by (6), where m is a product of the number N of times of irradiation of pulse excitation light and the average number $\mu$ of photons being incident in the time gate $\Delta T$.

$$m = \sum_{r=1}^{\infty} r \cdot p(r, \mu) \cdot N = \mu \cdot N \quad (6)$$

The correction unit 5a calculates (6) from the number N of times of irradiation of pulse excitation light input from the control unit 3 and the measured number k of photons input from the signal processing unit 4 and corrects the measured number k of photons to the number m of photons that are actually incident.

The correction unit 5a outputs the number of photons which is corrected from k to m to the fluorescence lifetime calculation unit 5b. The fluorescence lifetime calculation unit 5b calculates the fluorescence lifetime based on the number of photons m.

The correction unit 5a approximates (5) to a polynomial equation by a general method in place of calculation of (5) and calculates an approximate expression or calculates the value of the number μ of photons with respect to a count rate x in advance to form a table. In actual measurement, the table may be referred to without performing the calculation.

Plural time gates are set to be a first time gate ΔT1 and a second time gate ΔT2. It is assumed that the number of photons measured in the first time gate ΔT1 is represented by k1, and the number of photons measured in the second time gate ΔT2 is represented by k2. A time difference between the measurement start time of the first time gate ΔT1 and the measurement start time of the second time gate ΔT2 is represented by t. In this case, when the first time gate ΔT1 and the second time gate ΔT2 are identical, the fluorescence lifetime τ is expressed by:

$$\tau = \frac{t}{\ln(k1/k2)} \quad (7)$$

Figure 3:
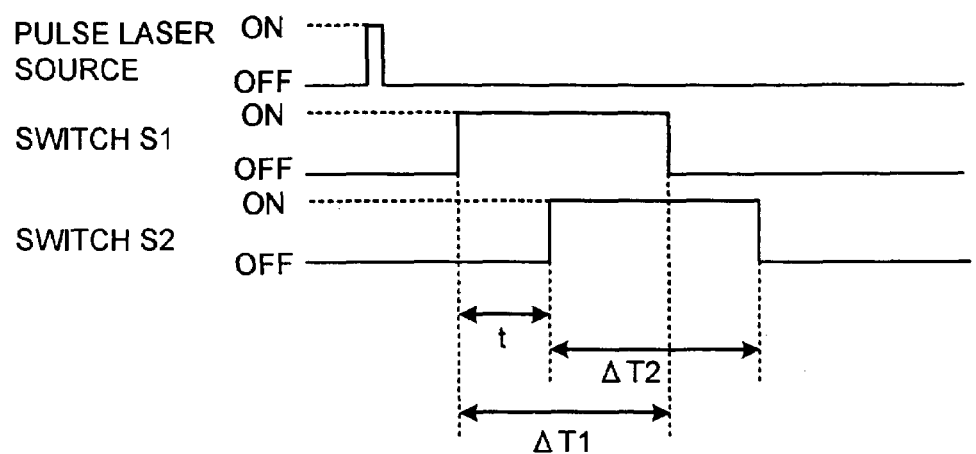
FIG. 3 is a timing chart for illustrating "ON" and "OFF" status of a pulse laser source and time gate switches of the fluorescence lifetime measurement apparatus according to the embodiment.

FIG. 3 is a timing chart for illustrating "ON" and "OFF" status of a pulse laser source and time gate switches S1 and S2 of the fluorescence lifetime measurement apparatus according to the embodiment. The control unit 3 controls the emission timing of a laser beam from the pulse laser source 2a of the measurement unit 2 and the switches S1 and S2 of the control unit 3 to set the first time gate ΔT1, the second time gate ΔT2, and a time difference t.

The correction unit 5a corrects the number k1 of photons measured by using (6) to m1. Similarly, the correction unit 5a corrects the number k2 into m2 and outputs the number m2 to the fluorescence lifetime calculation unit 5b. The fluorescence lifetime calculation unit 5b sets the number of photons being incident in the second time gate ΔT2 at m2. Then, (8) is employed to calculate the fluorescence lifetime τ.

$$\tau = \frac{t}{\ln(m1/m2)} \quad (8)$$

In this manner, the corrected number of photons is corrected in accordance with the Poisson distribution, and the fluorescence lifetime τ is calculated based on the corrected number of photons. In this case, even though the number of photons is measured in a time window in which a probability of emitting photons is high, a fluorescence lifetime having a small error of measurement can be calculated within a short time.

In (8), the numbers m1 and m2 obtained by correcting the numbers k1 and k2 are used. However, when the average numbers of photons being incident in the first time gate ΔT1 and the second time gate ΔT2 are given by μ1 and μ2, respectively, in single irradiation of pulse excitation light, the fluorescence lifetime τ can also be calculated from the average values μ1 and μ2 based on the relationship expressed by (6) without calculating m1 and m2.

Figure 4:
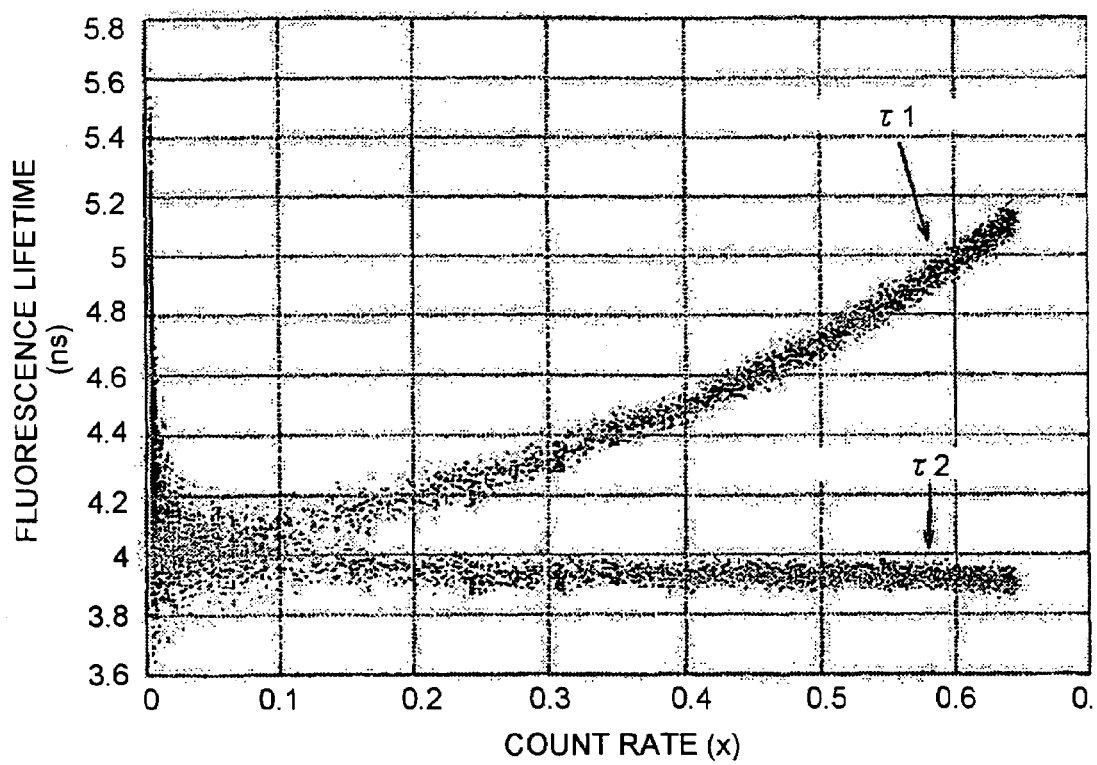
FIG. 4 is a graph of fluorescence life vs. count rate for illustrating an effect of correction.

FIG. 4 is a graph of fluorescence life vs. count rate for illustrating an effect of correction. The first time gate ΔT1 is set at 16 ns, the second time gate ΔT2 is set at 16 ns, and the time difference t is set at 16 ns, so that the fluorescence lifetime is calculated. Respective plots are performed based on a measurement result of 131,072-times irradiation of pulse excitation light and the number of photons. A set of the plots illustrated in FIG. 4 indicates a fluorescence lifetime τ1 calculated based on the number of photons which is not corrected and a fluorescence lifetime τ2 calculated based on the number of photons which is corrected.

The fluorescence lifetime τ2 corrected in FIG. 4 is 3.96 ns which is approximately constant regardless of the count rate x. On the other hand, the fluorescence lifetime τ1 which is not corrected increases with the increase of the count rate x. This means that when the count rate x is increased by increasing the probability of emitting photons, an error or measurement of photons increases. When the count rate x is increased, the number of photons measured in the first time gate ΔT1 is relatively smaller than the number of photons measured in the second time gate ΔT2. As a result, the fluorescence lifetime τ1 increases.

In contrast to this, when correction is performed, the distribution of the measured number of photons is corrected in accordance with the Poisson distribution to compensate for the error of measurement of the number of photons. For this reason, the calculated fluorescence lifetime τ2 is almost converged to a predetermined value independently of the count rate x. As a result, even though the energy of the pulse excitation light is increased to increase the probability of emitting photons, a fluorescence lifetime can be calculated independently of the count rate x. This means that a fluorescence lifetime having small error can be calculated within a short time.

Figure 5:
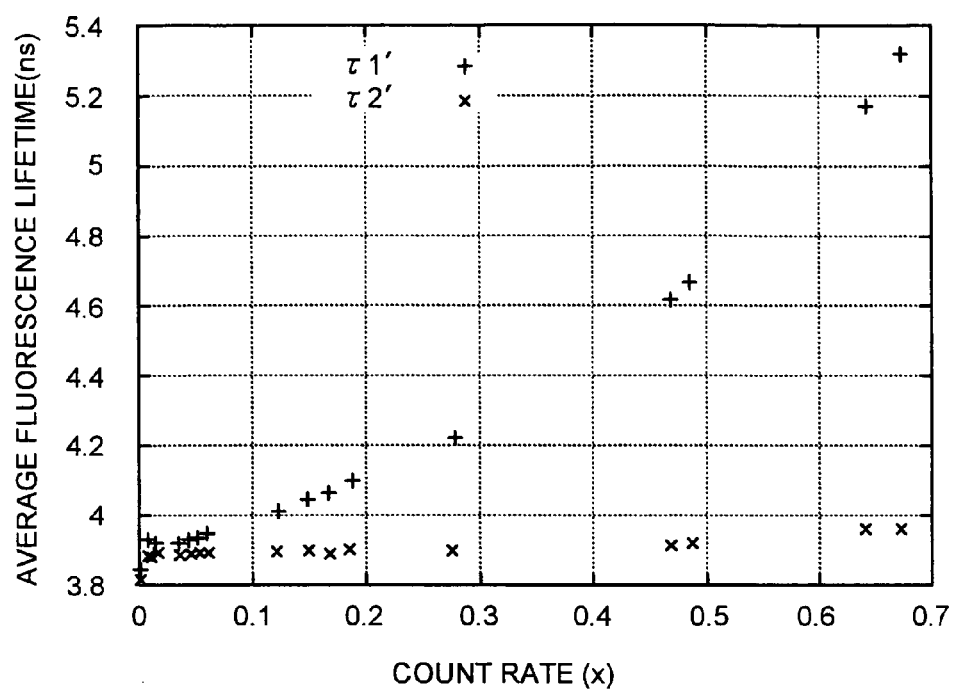
FIG. 5 is a graph of average fluorescence life vs. count rate for illustrating an effect of correction.

FIG. 5 is a graph of average fluorescence life vs. count rate for illustrating an effect of correction. Each plot indicates an average value obtained by the following manner. That is, 500,000-times irradiation of pulse excitation light and measurement of the number of photons are performed to calculate a fluorescence lifetime once, and the calculation of the fluorescence lifetime is performed 100 times. An average fluorescence lifetime τ1' calculated without correcting the measured number of photons and an average fluorescence lifetime τ2' calculated while correcting the number of photons are shown in FIG. 5. When the measured number of photons is not corrected, the calculated fluorescence lifetime increases with the increase of the count rate x to increase an error.

In this embodiment, the number of time gates is set at 2. However, when the number of time gates is 2, as is apparent from (8), only one fluorescence lifetime can be calculated from the number of photons. When a component of only one type of a fluorescent material is contained in a sample, measurement can be performed employing two time gates. However, fluorescent materials of plural types may be contained in the same sample, and these fluorescent materials frequently have a different fluorescence lifetime. When the fluorescence lifetime of plural fluorescent components contained in the sample are to be measured, the measurement is performed using at least three time gates. The measurement result is fitted by a function including a plurality of fluorescence lifetime components to calculate the fluorescence lifetime of the respective fluorescent components.

Since an event in which the respective components emit photons can be considered as an independent trial, probability distributions of the number of photons emitted from the components depend on the Poisson distribution.

At this time, when the average number of photons emitted from the $i^{th}$ component and being incident in a certain time gate per irradiation of pulse excitation light is represented by $\mu i$, a probability of the photons from the component i not being incident in the time gate can be expressed by:

$$p(0,\mu i)=e^{-\mu i} \quad (9)$$

Therefore, a probability of the photons from at least one component of the q components being incident on the time gate is represented by P, P can be expressed by:

$$p = 1 - p(0, \mu 1) \cdot p(0, \mu 2) \cdot p(0, \mu 3) \cdots p(0, \mu q) \quad (10)$$
$$= 1 - e^{-(\mu 1+\mu 2+\mu 3+\cdots+\mu q)}$$

In addition, when $\mu$ is expressed by:

$$\mu=\mu 1+\mu 2+\mu 3+\ldots+\mu q \quad (11),$$

the value $\mu$ is equal to the average number of photons emitted from all the fluorescent components and being incident in the time gate per irradiation of pulse excitation light, and the value P can be expressed by:

$$P=1-e^{-\mu} \quad (12)$$

When a count rate obtained when the measurement is actually performed in the time gate is represented by x, (13) is established.

$$p=x \quad (13)$$

From (12) and (13), (14) is derived.

$$\mu=-ln(1-x) \quad (14)$$

(14) is equivalent to (5). Even though the sample contains components having a plurality of fluorescence lifetimes, from the number of photons measured in plural time gates and the number of times of irradiation of pulse excitation light, the number of photons being incident in the time gates per irradiation of pulse excitation light or the number of photons actually being incident can be calculated.

Figure 6:
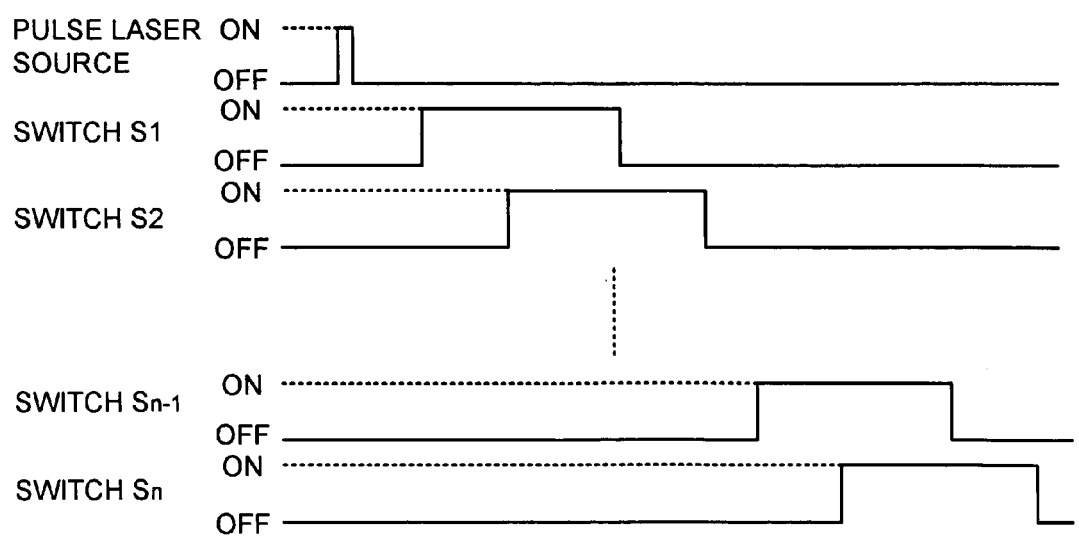
FIG. 6 is a timing chart for illustrating "ON" and "OFF" status of a pulse laser source and time gate switches of the fluorescence lifetime measurement apparatus according to a first modification of the embodiment.

In a case in which the sample contains components having a plurality of fluorescence lifetimes, n (n is 2 or more) switches may be arranged to set n time gates. FIG. 6 is a timing chart for illustrating "ON" and "OFF" status of a pulse laser source and time gate switches S1 to Sn of the fluorescence lifetime measurement apparatus according to a first modification of the embodiment. In this manner, when the time gate switches S1 to Sn are arranged, time gates $\Delta T1$ to $\Delta Tn$ can be set. When the number of time gates increases, the number of photons in the time gates can be accurately measured. As a result, a fluorescence lifetime can be more accurately calculated.

Figure 7:
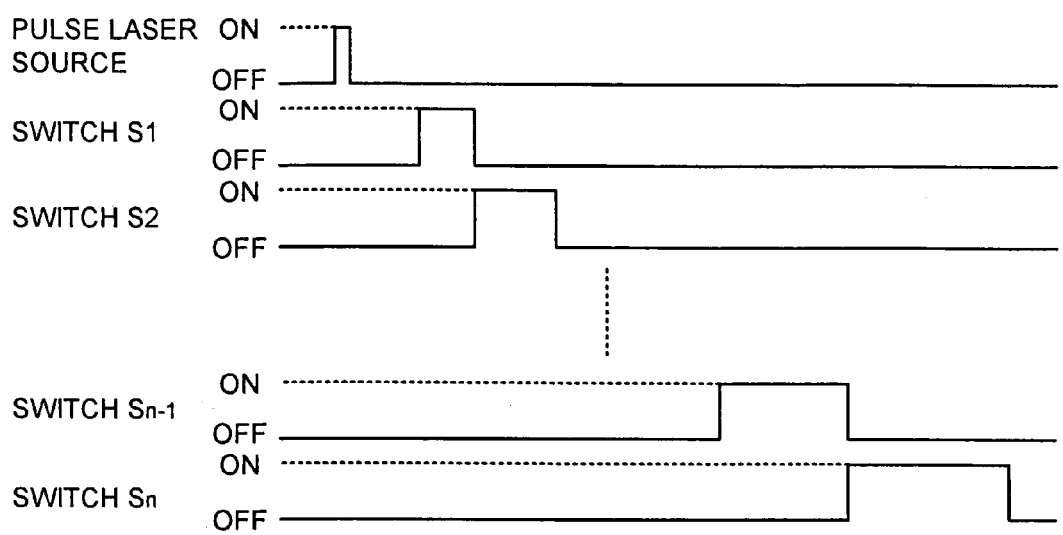
FIG. 7 is a timing chart for illustrating "ON" and "OFF" status of a pulse laser source and time gate switches of the fluorescence lifetime measurement apparatus according to a second modification of the embodiment.

FIG. 7 is a timing chart for illustrating "ON" and "OFF" status of a pulse laser source and time gate switches S1 to Sn of the fluorescence lifetime measurement apparatus according to a second modification of the embodiment. After the irradiation of pulse excitation light, the lengths of the time gates are increased over time. In this manner, the number of photons can be measured in accordance with the probability of emitting photons. More specifically, the errors of the measured number of photons are to be uniformed. As a result, the fluorescence lifetime can be accurately calculated.

Figure 8:
FIG. 8 is a timing chart for illustrating "ON" and "OFF" status of a pulse laser source and time gate switches of the fluorescence lifetime measurement apparatus according to a third modification of the embodiment.

FIG. 8 is a timing chart for illustrating "ON" and "OFF" status of a pulse laser source and time gate switches S1 to Sn of the fluorescence lifetime measurement apparatus according to a third modification of the embodiment. After the irradiation of pulse excitation light, the lengths of the time gates are increased over time, and time zones in which the number of photons are not performed are set between the time gates. In this manner, the number of photons is prevented from being measured in plural time gates, and the number of photons can be more accurately measured.

Although the invention has been described with respect to a specific embodiment for a complete and clear disclosure, the appended claims are not to be thus limited but are to be construed as embodying all modifications and alternative constructions that may occur to one skilled in the art which fairly fall within the basic teaching herein set forth.

What is claimed is:

1. An apparatus for measuring fluorescence lifetime, comprising:
   a pulse laser source that generates a pulse excitation light;
   an optical system that irradiates a sample with the pulse excitation light;
   a detector which detects a fluorescence emitted from the sample, and which outputs a detection signal corresponding to the fluorescence;
   a measurement unit which detects, based on the detection signal, whether the fluorescence is emitted for each of a plurality of time gates starting at different times, and which measures a number of photons of the fluorescence for each time gate;
   a correction unit which corrects, based on a predetermined probability distribution for a probability of emitting photons, at least one of: (i) the number of photons measured by the measurement unit for each time gate, and (ii) a first ratio of the number of photons measured by the measurement unit to a predetermined number of irradiations of the pulse excitation light into a second ratio, for each time gate; and
   a calculation unit that calculates a fluorescence lifetime of the sample based on at least one of the corrected number of photons and the second ratio.

2. The apparatus according to claim 1, wherein the predetermined probability distribution is Poisson distribution.

3. A method of measuring fluorescence lifetime, comprising:
   irradiating a sample with a pulse excitation light;
   detecting a fluorescence emitted from the sample, and outputting a detection signal corresponding to the fluorescence;
   detecting, based on the detection signal, whether the fluorescence is emitted for each of a plurality of time gates starting at different times;
   measuring a number of photons of the fluorescence for each time gate;
   correcting, based on a predetermined probability distribution for a probability of emitting photons, at least one of: (i) the measured number of photons for each time gate, and (ii) a first ratio of the measured number of photons to a predetermined number of irradiations of the pulse excitation light into a second ratio, for each time gate; and calculating a fluorescence lifetime based on at least one of the corrected number of photons and the second ratio.

4. The method according to claim 3, wherein the predetermined probability distribution is Poisson distribution.

* * * * *